(12) United States Patent
Yang et al.

(10) Patent No.: US 11,541,895 B2
(45) Date of Patent: Jan. 3, 2023

(54) DRIVING ASSISTANCE SYSTEM AND DRIVING ASSISTANCE METHOD

(71) Applicant: Industrial Technology Research Institute, Hsinchu (TW)

(72) Inventors: Ming-Huan Yang, Hsinchu (TW); Kuang-Ching Fan, Hsinchu County (TW); Cheng-Chung Lee, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 363 days.

(21) Appl. No.: 16/831,838

(22) Filed: Mar. 27, 2020

(65) Prior Publication Data

US 2020/0317210 A1   Oct. 8, 2020

Related U.S. Application Data

(60) Provisional application No. 62/828,488, filed on Apr. 3, 2019.

(30) Foreign Application Priority Data

Jan. 8, 2020   (TW) .................................. 109100565

(51) Int. Cl.
*G01C 22/00*    (2006.01)
*B60W 40/08*    (2012.01)
(Continued)

(52) U.S. Cl.
CPC .......... *B60W 40/08* (2013.01); *A61B 5/02416* (2013.01); *A61B 5/282* (2021.01);
(Continued)

(58) Field of Classification Search
CPC ............. B60W 40/08; B60W 60/0016; B60W 60/0051; B60W 50/14; B60W 2540/221;
(Continued)

(56) References Cited

U.S. PATENT DOCUMENTS 5,944,022 A * 8/1999 Nardella ............. A61B 5/0536
                                                   128/899
6,104,296 A * 8/2000 Yasushi ................. A61B 5/282
                                                   701/1
(Continued)

FOREIGN PATENT DOCUMENTS

CN     105144199    12/2015
CN     106163387    11/2016
(Continued)

OTHER PUBLICATIONS

Office Action of China Counterpart Application, dated Mar. 26, 2021, pp. 1-12.
(Continued)

*Primary Examiner* — Zhen Y Wu
(74) *Attorney, Agent, or Firm* — JCIPRNET

(57) ABSTRACT

A driving assistance system and a driving assistance method are provided. The driving assistance system includes a physiological information sensing system, an external physical symptom detection system, and a processing device. The physiological information sensing system is configured to sense physiological information of a driver. The external physical symptom detection system is configured to detect an external physical symptom of the driver. The processing device is coupled to the physiological information sensing system and the external physical symptom detection system. When the physiological information of the driver and the external physical symptom of the driver are abnormal, the processing device initiates an emergency procedure.

19 Claims, 14 Drawing Sheets

(51) Int. Cl.
*B60W 50/14* (2020.01)
*B60W 60/00* (2020.01)
*A61B 5/024* (2006.01)
*A61B 5/00* (2006.01)
*A61B 5/282* (2021.01)
*A61B 5/0531* (2021.01)
*A61B 5/11* (2006.01)

(52) U.S. Cl.
CPC .......... *A61B 5/6893* (2013.01); *A61B 5/7282* (2013.01); *A61B 5/746* (2013.01); *A61B 5/747* (2013.01); *B60W 50/14* (2013.01); *B60W 60/0016* (2020.02); *B60W 60/0051* (2020.02); *A61B 5/0531* (2013.01); *A61B 5/1123* (2013.01); *A61B 5/4803* (2013.01); *A61B 2562/0247* (2013.01); *B60W 2040/0872* (2013.01); *B60W 2422/95* (2013.01); *B60W 2540/221* (2020.02)

(58) Field of Classification Search
CPC ...... B60W 2040/0872; B60W 2422/95; A61B 5/282; A61B 5/02416; A61B 5/6893; A61B 5/7282; A61B 5/746; A61B 5/757; A61B 5/0531; A61B 5/1123; A61B 5/4803; A61B 2562/0247
USPC .......................................................... 701/26
See application file for complete search history.

(56) References Cited

U.S. PATENT DOCUMENTS

| | | | | |
|---|---|---|---|---|
| 6,496,721 | B1* | 12/2002 | Yonce | A61B 5/30 600/509 |
| 8,822,309 | B2 | 9/2014 | Pan | |
| 9,751,534 | B2* | 9/2017 | Fung | G06V 10/764 |
| 9,848,814 | B2 | 12/2017 | Benson et al. | |
| 10,434,947 | B2* | 10/2019 | Zafeirakis | B60R 21/01552 |
| 2011/0288424 | A1* | 11/2011 | Kanai | A61B 5/024 600/500 |
| 2012/0212353 | A1* | 8/2012 | Fung | B60W 10/18 701/1 |
| 2012/0330173 | A1* | 12/2012 | Park | A61B 5/18 600/509 |
| 2013/0171599 | A1* | 7/2013 | Bleich | G16H 20/30 434/247 |
| 2015/0314792 | A1* | 11/2015 | Kalhous | B60R 16/037 701/1 |
| 2016/0001781 | A1* | 1/2016 | Fung | G16H 50/20 701/36 |
| 2017/0181713 | A1* | 6/2017 | Feng | A61B 5/0205 |
| 2018/0146870 | A1* | 5/2018 | Shemesh | A61B 5/02416 |
| 2018/0225437 | A1 | 8/2018 | Suh et al. | |
| 2018/0253094 | A1* | 9/2018 | Chang | G05D 1/0055 |
| 2018/0296157 | A1* | 10/2018 | Bleich | A61B 7/00 |
| 2019/0047588 | A1* | 2/2019 | Yabuuchi | B60W 60/0057 |
| 2019/0082993 | A1* | 3/2019 | Choi | A61B 5/282 |
| 2019/0099118 | A1* | 4/2019 | Patel | A61B 5/6893 |
| 2019/0161091 | A1* | 5/2019 | An | B60K 28/06 |
| 2019/0213429 | A1* | 7/2019 | Sicconi | G06F 3/0346 |
| 2019/0241191 | A1* | 8/2019 | Wu | A61B 5/1116 |
| 2019/0276032 | A1* | 9/2019 | Fung | G06V 40/70 |

FOREIGN PATENT DOCUMENTS

| | | |
|---|---|---|
| CN | 106231008 | 12/2016 |
| CN | 106462027 | 2/2017 |
| CN | 109410524 | 3/2019 |
| KR | 101554188 | 9/2015 |
| TW | M560102 | 5/2018 |
| WO | 2014068892 | 5/2014 |

OTHER PUBLICATIONS

"Office Action of Taiwan Counterpart Application", dated Nov. 20, 2020, p. 1-p. 15.

* cited by examiner

DRIVING ASSISTANCE SYSTEM AND DRIVING ASSISTANCE METHOD

CROSS-REFERENCE TO RELATED APPLICATION

This application claims the priority benefits of U.S. provisional application Ser. No. 62/828,488, filed on Apr. 3, 2019 and Taiwan application no. 109100565, filed on Jan. 8, 2020. The entirety of each of the above-mentioned patent applications is hereby incorporated by reference herein.

TECHNICAL FIELD

The disclosure relates to an assistance system and an assistance method, and also relates to a driving assistance system and a driving assistance method.

BACKGROUND

In recent years, with the increasing maturity of vehicle technologies, vehicles have become popular around the world. Although vehicles bring convenience to people's life, the number of casualties caused by traffic accidents remains high. In most traffic accidents, drivers are held accountable, and traffic accidents are mostly due to drivers' driving under influence, speeding, or physiological issues such as experiencing a heart attack or dozing off. If physical issues of drivers that happen suddenly cannot be detected and taken care of immediately, such issues may very likely cause traffic accidents that cause damages.

SUMMARY

According to an embodiment of the disclosure, a driving assistance system, includes a physiological information sensing system configured to sense physiological information of a driver; an external physical symptom detection system configured to detect an external physical symptom of the driver; and a processing device coupled to the physiological information sensing system and the external physical symptom detection system. When the physiological information of the driver and the external physical symptom of the driver are abnormal, the processing device initiates an emergency procedure.

According to another embodiment of the disclosure, a driving assistance method includes: detecting physiological information of a driver; detecting an external physical symptom of the driver; and initiating an emergency procedure when the physiological information of the driver and the external physical symptom of the driver are abnormal.

According to another embodiment of the disclosure, a driving assistance system includes: a physiological information sensing system configured to sense physiological information of a driver; and a processing device coupled to the physiological information sensing system. When the physiological information of the driver is abnormal, the processing device initiates an emergency procedure. The physiological information sensing system includes a plurality of physiological information sensing modules, a microcontroller, and a switching circuit. The physiological information sensing modules are configured in at least one operation portion of a vehicle and coupled to the switching circuit, the microcontroller is coupled to the switching circuit and the processing device, and the microcontroller controls the switching circuit to transmit, to the processing device, the physiological information detected by the physiological information sensing module that is configured in the at least one operation portion and that is in contact with the driver. Each of the physiological information sensing modules includes an electrocardiogram (ECG) sensor, a photoplethysmogram (PPG) sensor, and a compensation module, and the microcontroller chooses to perform ECG sensing mode measurement or PPG sensing mode measurement through the switching circuit.

Based on the above, in the driving assistance system and the driving assistance method in the embodiments of the disclosure, both the physiological information of the driver and the external physical symptom of the driver are detected, so the emergency procedure can be immediately and accurately initiated to reduce the probability of an accident. Alternatively, in the driving assistance system and the driving assistance method in the embodiments of the disclosure, the ECG sensing mode measurement or the PPG sensing mode measurement can be automatically switched, so the access to physiological information can be ensure via the PPG sensing mode measurement, and the accuracy can be increased via the ECG sensing mode measurement.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

Figure 1:
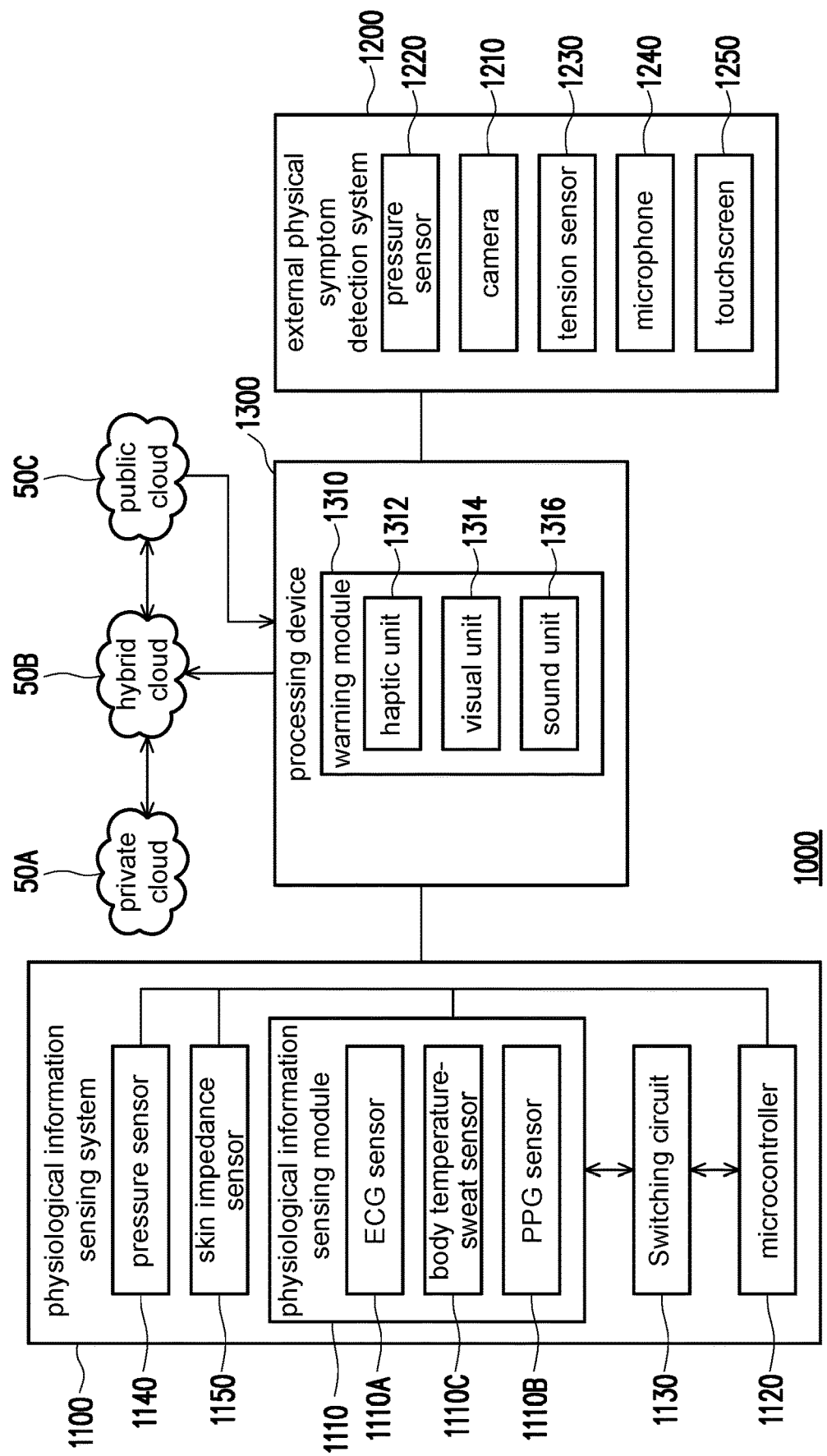
FIG. 1 is a schematic diagram of an architecture of a driving assistance system according to an embodiment of the disclosure.

FIG. 1 is a schematic diagram of an architecture of a driving assistance system according to an embodiment of the disclosure. Referring to FIG. 1, a driving assistance system 1000 in the present embodiment includes a physiological information sensing system 1100, an external physical symptom detection system 1200, and a processing device 1300. The physiological information sensing system 1100 is configured to sense physiological information of a driver. The physiological information includes but is not limited to an ECG, a PPG, a body temperature, and sweat. The external physical symptom detection system 1200 is configured to detect an external physical symptom of the driver. The processing device 1300 is coupled to the physiological information sensing system 1100 and the external physical symptom detection system 1200.

Figure 2A:
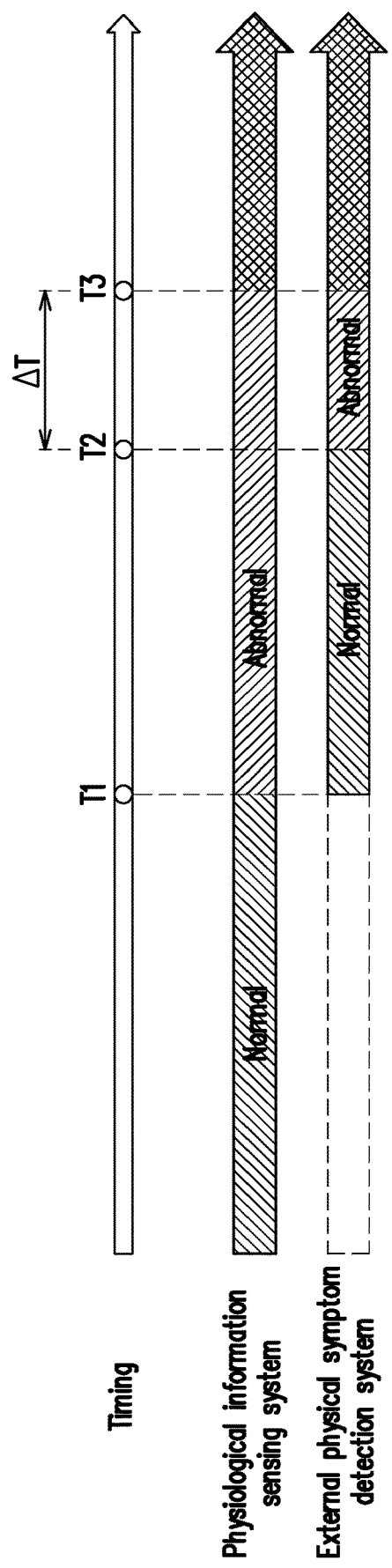
FIG. 2A is a timing diagram of a driving assistance method according to an embodiment of the disclosure.

FIG. 2A is a timing diagram of a driving assistance method according to an embodiment of the disclosure. Referring to FIG. 1 and FIG. 2A, in the driving assistance system 1000 and the driving assistance method in the present embodiment, when the physiological information of the driver is abnormal, that is, at a time T1, the processing device 1300 activates the external physical symptom detection system 1200 to detect the external physical symptom of the driver. When the external physical symptom of the driver is abnormal, at a time T2, the processing device 1300 initiates an emergency procedure.

It can be learned from the above that in the driving assistance system 1000 and the driving assistance method in the present embodiment, the physiological information sensing system 1100 may continuously monitor the physiological information of the driver in real time. Once the physiological information is abnormal, the external physical symptom detection system 1200 may further detect the external physical symptom of the driver to determine what kind of physical discomfort the driver has. Therefore, the processing device 1300 may initiate an appropriate emergency procedure based on a result of the determining, to avoid mistakenly initiating the emergency procedure due to a temporary abnormality of the physiological information. The result of the determining may be sent to a hospital, a police unit, or other emergency units to give a fastest and correct assistance to the driver. In addition, in the driving assistance system 1000 and the driving assistance method in the present embodiment, an ECG and a PPG are detected at the same time. Even if an ECG single-lead circuit cannot be formed because the driver operates or turns a steering wheel with one hand, basic physiological information such as a heart rate can be obtained through the PPG.

In addition, in the driving assistance method in the present embodiment, in addition to directly initiating the emergency procedure at the time T2, the processing device 1300 may initiate the emergency procedure when the external physical symptom of the driver is abnormal (the time T2) and after the abnormality lasts for a preset period of time ΔT, that is, at a time T3. A probability of misjudgment can be reduced by setting the preset time (ΔT). In addition, although an example in which the external physical symptom detection system 1200 is activated at the time T1 is used, the external physical symptom detection system 1200 can be always activated as the physiological information sensing system 1100.

The ECG is used to record an electrophysiological activity of the heart through the thorax in units of time and detect a potential change of the heart through a skin-contacting electrode. A result of the ECG is usually displayed in a wave pattern. The heart rate can be obtained from the ECG, and is basically calculated based on a time interval between R waves in the ECG. When the time interval between R waves is larger, the heart rate is lower, and when the time interval between R waves is smaller, the heart rate is higher. In addition, a heart rhythm can also be obtained from the ECG. The heart rate is a number of heartbeats per minute, and the heart rhythm is a rhythm of heartbeats. The PPG is a non-invasive method for detecting a change in a blood volume in living tissues via photoelectric means. When a light beam with a certain wavelength is irradiated on a skin surface, contraction and expansion of blood vessels 20 affect transmission or reflection of the light during each heartbeat. When the light beam passes through the skin tissue and then reflects to a light receiver, an amount of light is attenuated, and the change in the amount of light is related to a change in an amount of blood in an artery caused by the heartbeat. Therefore, information such as the heart rate and a blood pressure can be obtained by analysing the change in the amount of light.

When the driver needs to normally operate various types of vehicles such as a car, a ship, or an airplane, a brain of the driver needs blood to provide nutrients and oxygen. When there is insufficient blood in the brain, the driver may be suddenly unconscious. Therefore, a physical condition of the driver may be preliminarily determined by detecting the physiological information of the driver such as the ECG and the PPG.

Figure 3:
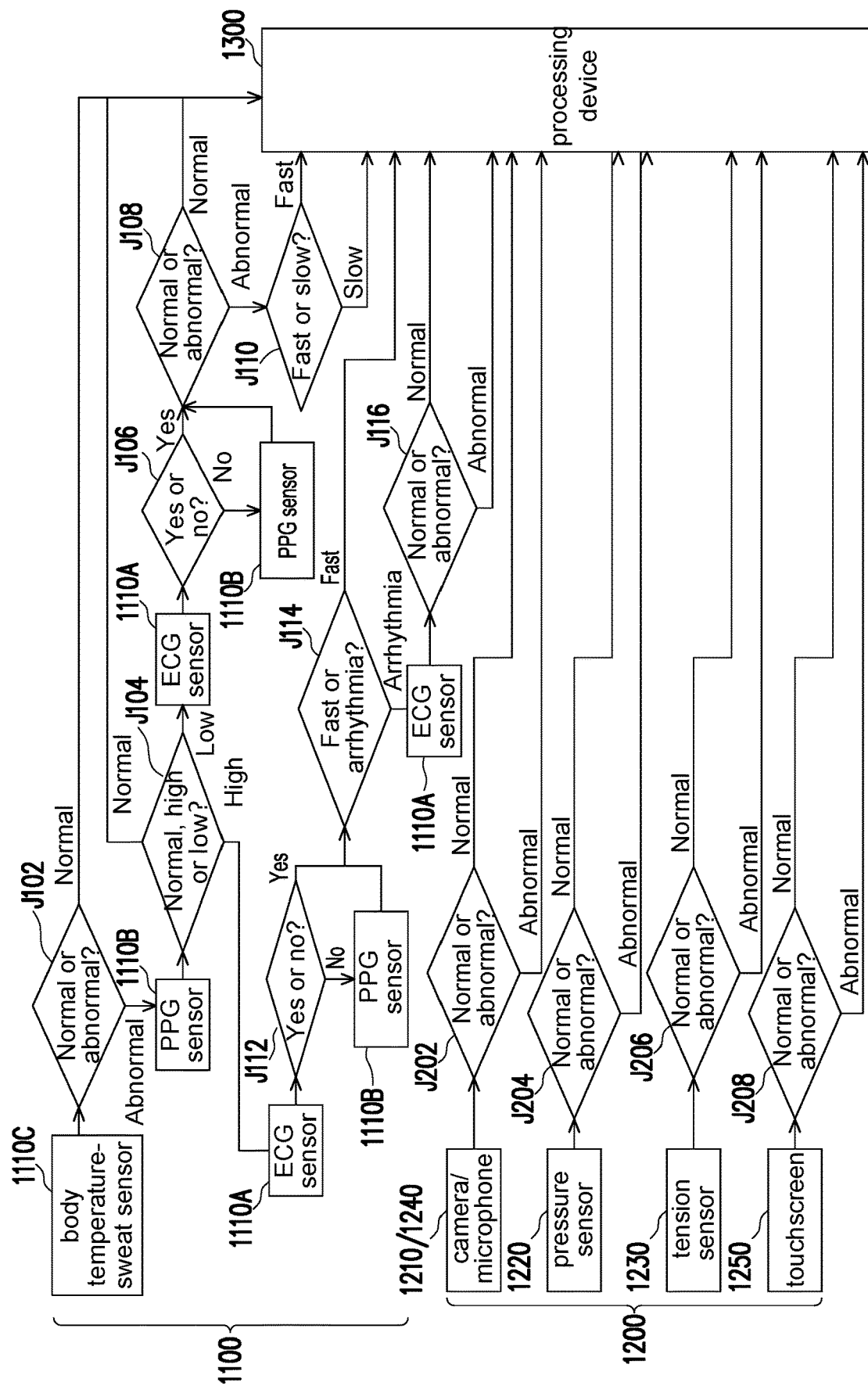
FIG. 3 is a flowchart of the driving assistance method in FIG. 2A.

FIG. 3 is a flowchart of the driving assistance method in FIG. 2A. Referring to FIG. 1 and FIG. 3, for example, the physiological information sensing system 1100 may further include a body temperature-sweat sensor 1110C. If it is determined at block J102 that a body temperature of the driver is normal and sweat is normal based on a sensing result of the body temperature-sweat sensor 1110C, that is, the body temperature of the driver is normal and a sweat level is normal, information indicating that the condition of the driver is normal is transmitted to the processing device 1300. In addition, if it is determined at block J102 that the body temperature of the driver is normal but the sweating is abnormal, that is, the driver is in a cold sweat, or there are other conditions of an abnormal body temperature and/or abnormal sweating, a blood pressure level is determined at block J104 based on the PPG provided by a PPG sensor 1110B of the physiological information sensing system 1100. If it is determined at block J104 that the blood pressure is low, based on whether an ECG sensor 1110A of the physiological information sensing system 1100 can provide an ECG, it is determined at block J106 whether the ECG sensor 1110A forms a loop. If it is determined at block J106 that the ECG sensor 1110A forms a loop, the ECG provided by the ECG sensor 1110A may be used to determine a heart rhythm status at block J108. If it is determined at block J108 that the heart rhythm status is normal, information indicating that the driver is in a normal state is transmitted to the processing device 1300. If it is determined at block J108 that the heart rhythm status is abnormal, information indicating that the heart rhythm status of the driver determined at block J110 is fast or slow is transmitted to the processing device 1300.

If it is determined at block J106 that the ECG sensor 1110A does not form a loop, the PPG provided by the PPG sensor 1110B is used to determine the heart rhythm status at block J108. If it is determined at block J104 that the blood pressure is high, based on whether the ECG sensor 1110A can provide an ECG, it is determined at block J112 whether the ECG sensor 1110A forms a loop. If it is determined at block J112 that the ECG sensor 1110A forms a loop, the ECG provided by the ECG sensor 1110A may be used to determine a heart rhythm status at block J114. If it is determined at block J114 that the heart rhythm is too fast, the heart rate status of the driver is transmitted to the processing device 1300. If arrhythmia is determined at block J114, it may be determined at block J116 whether the ECG provided by the ECG sensor 1110A is normal. If it is determined at block J116 that the ECG is normal, information indicating that the driver is in a normal state is transmitted to the processing device 1300. If it is determined at block J116 that the ECG is abnormal, information indicating that the ECG of the driver is abnormal is transmitted to the processing device 1300. In addition, if it is determined at block J112 that the ECG sensor 1110A does not form a loop, the PPG provided by the PPG sensor 1110B is used to determine the heart rhythm status at block J114.

In addition, the external physical symptom detection system 1200 in the present embodiment may include a camera 1210, a pressure sensor 1220, a tension sensor 1230, a microphone 1240, and a touchscreen 1250. However, in other embodiments, the external physical symptom detection system 1200 may include only some of the foregoing components or other components that can detect the external physical symptom. At block J202, it may be determined whether the driver has twitch, a twisted face, a wry mouth, chest fondling, cracked eyes, an abnormal tone, or other abnormal images and sounds based on detection results of the camera 1210 and the microphone 1240. At block J204, it may be determined, based on a detection result of the pressure sensor 1220, whether the driver is subject to strong impact, unilateral weakness, restlessness, general weakness, or other abnormal external physical symptoms determined based on the pressure detection result. The pressure sensor 1220 is, for example, a section mounted on a driver's seat or a seat belt that is mainly in contact with the driver. At block J206, it may be determined, based on a detection result of the tension sensor 1230, whether the driver has a strong twitch, a unilateral tilt, a tilting twist, a slow motion, or other abnormal external physical symptoms determined based on the tension detection result. At block J208, it may be determined, based on a detection result of the touchscreen 1250, whether the external physical symptom of the driver is abnormal due to irregular use of the touchscreen 1250 such as multipoint random touching. In addition, the touchscreen 1250 may be replaced by an element having only a touch sensing function but no display function. In summary, the external physical symptom detection system 1200 is configured to detect at least one of an expression, a gesture, speech, an action, or other external physical symptoms.

Determining results at blocks J202, J204, J206, and J208 are all transmitted to the processing device 1300. After combining the information provided by the physiological information sensing system 1100 with the information provided by the external physical symptom detection system 1200, the processing device 1300 may further determine whether the driver is normal or has other diseases. For example, when the body temperature of the driver is normal but has sweating, a high blood pressure, and a fast heart rate and is accompanied by external physical symptoms such as convulsion, strong impact, violent twitching, dizziness, irregular touch, a repeated action, and barking, it indicates that the driver may have epilepsy. When the body temperature of the driver is normal but has sweating, a high blood pressure, and arrhythmia, and the ECG is normal but is accompanied by external physical symptoms such as a twisted face, a wry mouth, dizziness, unilateral weakness, a unilateral tilt, and irregular touch, it indicates that the driver may have a stroke. When the body temperature of the driver is normal but has sweating, a high blood pressure, and arrhythmia, and the ECG is abnormal and is accompanied by external physical symptoms such as chest fondling, angina pectoris, left and right interactive tilting and twisting of a sitting posture, panting, a chest pain, restlessness, an abnormal tone, and irregular touch, it indicates that the driver may have a psychogenic illness. For example, when the body temperature of the driver is normal but has sweating, a low blood pressure, and a fast heart rate and is accompanied by external physical symptoms such as shivering, general weakness, a slow action, an abnormal tones, and irregular touch, it indicates that the driver may have hypoglycaemia. For example, when the body temperature of the driver is normal but has sweating, a low blood pressure, and a slow heart rate and is accompanied by external physical symptoms such as cracked eyes, general weakness, a slow action, an abnormal tone, and irregular touch, it indicates that the driver may have vagus nerve stimulation, that is, frightened. For example, a high blood pressure is higher than 140 millimeters of mercury (mmHg), a low blood pressure is lower than 90 mmHg, a fast heart rate is higher than 100 beats per minute (min), and a slow heart rate is lower than 60 beats per minute. Arrhythmia is heart rate variability, that is, a difference between heartbeats is greater than 50 milliseconds (msec).

After the processing device 1300 determines a disease of the driver more accurately, an appropriate emergency procedure may be initiated, for example, issuing a warning, initiating autonomous driving, pulling over, sending to a medical emergency or other appropriate emergency procedures. Referring to FIG. 1 again, a private cloud 50A of the driver may transmit basic data of the driver to a hybrid cloud 50B. The basic information of the driver is, for example, basic physiological information, a medical examination report, or a special medical history. The processing device 1300 may also transmit detection results of the physiological information sensing system 1100 and the external physical symptom detection system 1200 to the hybrid cloud 50B. The hybrid cloud 50B may transmit the foregoing information to a public cloud 50C of a hospital, a police station, or other emergency units to give fastest and correct assistance to the driver. For example, the hospital may learn that the driver is sent to the hospital and prepare an appropriate medical procedure based on the information received before the driver arrives at the hospital. Certainly, route planning is also included in the part of starting autonomous driving, and details are not described herein.

In addition, the processing device 1300 may further include a warning module 1310, to warn the driver or a nearby pedestrian when the physiological information of the driver or the external physical symptom of the driver is abnormal. For example, the alarm warning module 1310 may include a haptic unit 1312, a visual unit 1314, and a sound unit 1316. The haptic unit 1312 generates alertness by vibrating the driver's seat or through other methods that can make the driver have a tactile response. The visual unit 1314, for example, generates alertness by flashing a light on a dashboard or through other methods that can make the driver have a visual response, or may activate an external flashing light of a vehicle to alert a driver or a nearby pedestrian. The sound unit 1316, for example, generates alertness by activating a buzzer to emit a sound or through other methods that can make the driver have an audible response, or may activate a horn of a vehicle to warn a driver or a nearby pedestrian around.

In an embodiment, the physiological information sensing system 1100 and the external physical symptom detection system 1200 may simultaneously and continuously monitor the physiological information of the driver and the external physical symptom of the driver in real time. Alternatively, as shown in the timing diagram in FIG. 2A, the physiological information sensing system 1100 is activated first. Then, when the physiological information of the driver is abnormal, the processing device 1300 activates the external physical symptom detection system 1200 to detect the external physical symptom of the driver. The processing device 1300 determines, based on the physiological information of the driver or the external physical symptom of the driver, a timing for initiating the emergency procedure and a processing manner. For example, the emergency procedure may be initiated immediately when the physiological information or the external physical symptom is abnormal and it is determined that the driver cannot or should not continue driving, instead of initiating the emergency procedure after the abnormality lasts for a period of time, as shown in FIG. 2A.

Figure 2B:
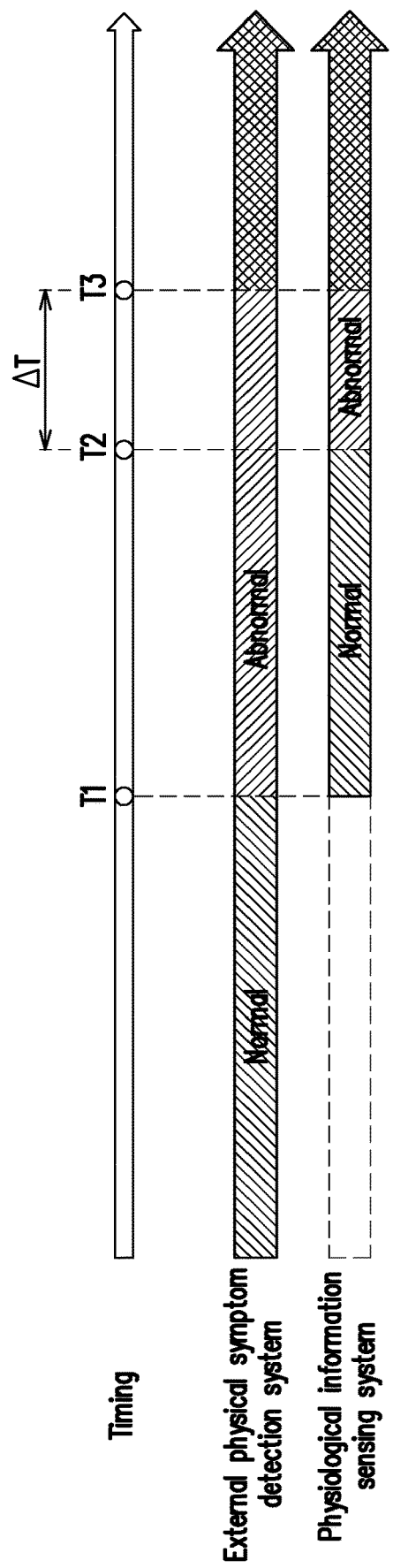
FIG. 2B is a timing diagram of a driving assistance method according to another embodiment of the disclosure.

FIG. 2B is a timing diagram of a driving assistance method according to another embodiment of the disclosure. As shown in the timing diagram in FIG. 2B, in another embodiment, the external physical symptom detection system 1200 in FIG. 1 may be activated first. Then, when an abnormal external physical symptom of the driver is observed at a time T1, the processing device 1300 in FIG. 1 activates the physiological information sensing system 1100 to obtain the physiological information, thereby determining whether the driver cannot or should not continue driving. For example, at a time T2, when the physiological information of the driver is abnormal, the processing device 1300 may further activate the emergency procedure.

Figure 4:
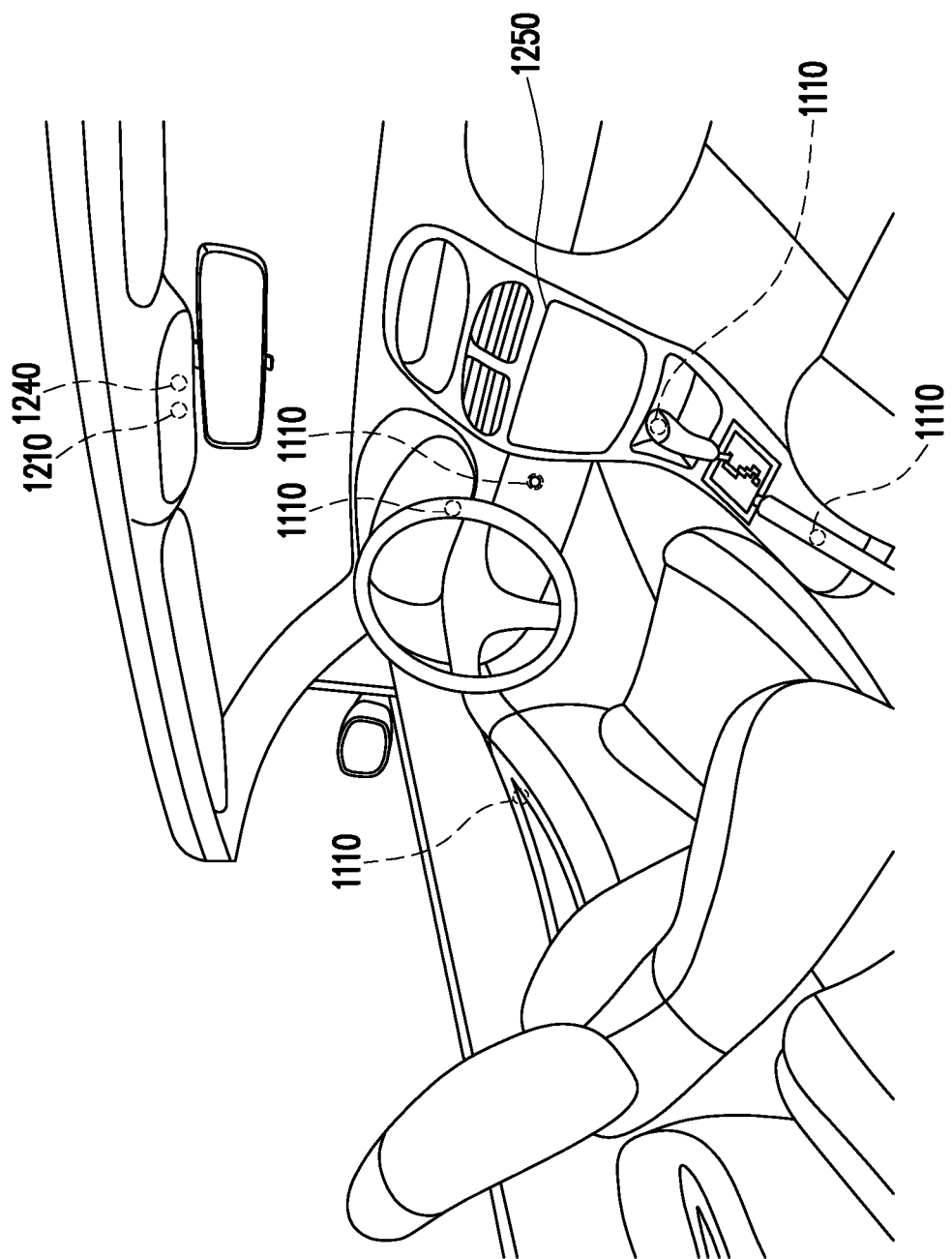
FIG. 4 is a schematic configuration diagram of the driving assistance system in FIG. 1.

FIG. 4 is a schematic configuration diagram of the driving assistance system in FIG. 1. Referring to FIG. 1 and FIG. 4, in the present embodiment, the physiological information sensing system 1100 includes a plurality of physiological information sensing modules 1110, a microcontroller 1120, and a switching circuit 1130. The plurality of physiological information sensing modules 1110 are configured in at least one operation portion of a vehicle (shown in FIG. 4) and coupled to the switching circuit 1130. The microcontroller 1120 is coupled to the switching circuit 1130 and the processing device 1300. The microcontroller 1120 controls the switching circuit 1130 to transmit, to the processing device 1300, the physiological information detected by the physiological information sensing module 1110 that is configured in the operation portion and that is in contact with the driver. For example, components shown in FIG. 4 that can be used as the operation portion of the vehicle include at least a steering wheel, a start button, a gear stick, a cockpit door, a hand brake, and the like, but may further include other parts that are commonly touched by the driver. The plurality of physiological information sensing modules 1110 are configured in a plurality of operation parts of the vehicle, so that the physiological information can be detected when the driver has different driving habits. For example, when hands of the driver hold the steering wheel, two of the plurality of physiological information sensing modules 1110 that are placed on the steering wheel and that are in contact with the driver can provide the required physiological information. Alternatively, when the driver holds the steering wheel with only one hand and is in contact with the start button, the gear stick, the cockpit door, or the hand brake with the other hand, one physiological information sensing module 1110 that is placed on the steering wheel and that is in contact with the driver and one physiological information sensing module 1110 placed on another operation part can also provide the required physiological information. Even when the driver does not hold the steering wheel with the hands, two physiological information sensing modules 1110 that are placed on the start button, the gear stick, the cockpit door, or the hand brake and that are in contact with the driver can provide the required physiological information. Through the microcontroller 1120 and the switching circuit 1130, it can be quickly determined which physiological information sensing module 1110 configured in which operation part can provide the physiological information. In addition, FIG. 4 also illustrates positions at which the camera 1210, the microphone 1240, and the touchscreen 1250 of the external physical symptom detection system 1200 can be mounted, but the disclosure is not limited thereto.

Figure 5:
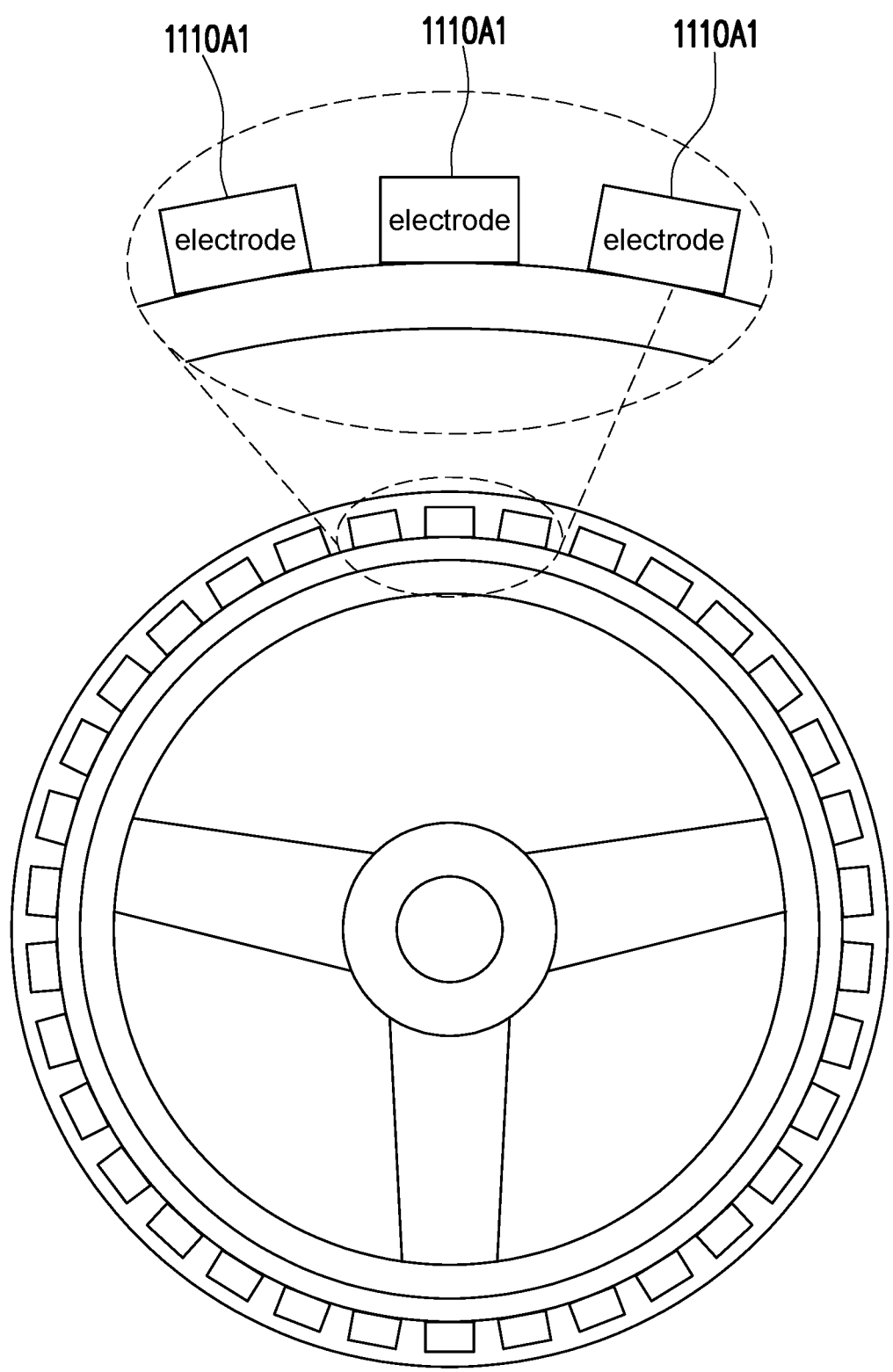
FIG. 5 is a schematic configuration diagram of a sensor of a part of the driving assistance system in FIG. 1.

FIG. 5 is a schematic configuration diagram of a sensor of a part of the driving assistance system in FIG. 1. Referring to FIG. 1 and FIG. 5, in the present embodiment, the physiological information sensing system 1100 includes an ECG sensor 1110A. A plurality of first electrodes 1110A1 of the ECG sensor 1110A are configured on a steering wheel of a vehicle and include at least three of the plurality of first electrodes 1110A1 within a range 70 mm. An average height of a human female is 1.6 meters, a palm length is 171 mm, and a palm width is 73 mm. An average height of a human male is 1.75 meters, a palm length is 188 mm, and a palm width is 83 mm. According to the above design, it can be ensured that at least one palm of a male or female driver can touch three or more first electrodes 1110A1. The first electrode 1110A1 that is fully touched serves as a sensing electrode of the ECG sensor 1110A during the current detection.

Figure 6:
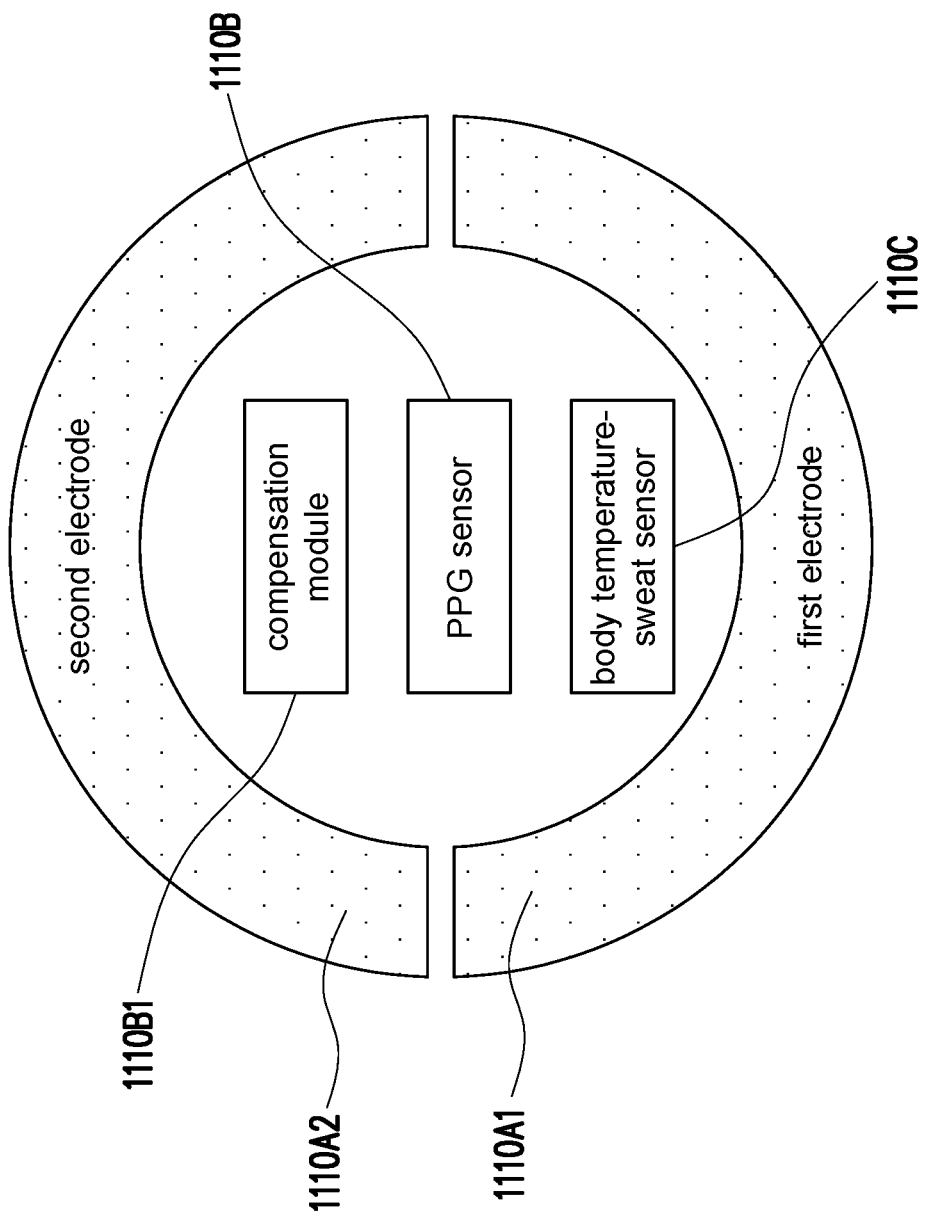
FIG. 6 is a schematic diagram of a physiological signal sensing module of the driving assistance system in FIG. 1.

FIG. 6 is a schematic diagram of a physiological signal sensing module of the driving assistance system in FIG. 1. This module may be configured on the steering wheel, the start button, the gear stick, the cockpit door, the hand brake, or other parts that are commonly touched by the driver. Referring to FIG. 1, FIG. 5 and FIG. 6, in the present embodiment, similar to the first electrodes 1110A1, a plurality of second electrodes 1110A2 of the ECG sensor 1110A may also be configured on the steering wheel of the vehicle and includes at least three of the plurality of second electrodes 1110A2 within a range of 70 mm. The first electrode 1110A1 and the second electrode 1110A2 that are in contact with the driver may constitute a signal-lead ECG sensor 1110A. Based on easy installation and quality assurance, the foregoing sensors may be modularized. In the module in FIG. 6, a compensation module 1110B1 may be disposed. The compensation module 1110B1 may be a skin impedance sensor 1150, a pressure sensor 1140, a compensation unit (a phase retarder, a photointerrupter, or an RC retarder), or the like in FIG. 1. The processing device 1300 may use the compensation module 1110B1 to correct a sensing result of the physiological information sensing module 1110. For example, skin's electrical conductivity is affected by dryness of an environment, resulting in a change in a resistance of the hands in contact with the steering wheel, and further affecting accuracy of single-lead ECG measurement. By measuring the skin impedance value, the ECG may be corrected through table lookup or may be linearly corrected.

In addition, as driver's degree of exertion is different, blood vessels 20 in a tested area are deformed, thereby resulting in a decrease in a volume of the blood vessels 20, and further reducing signal strength detected by the PPG sensor 1110B. Further, when a cross section of a blood vessel 20 is approximately circular, if a length of the blood vessel 20 is L, and a radius of the cross section of the blood vessel 20 is r, a volume of the blood vessel 20 detected by the PPG sensor 1110B is about $\pi r^2 L$. When the driver exerts more force and a cross section of a blood vessel 20 is approximately oval, if a length of the blood vessel 20 is L, a semi-major axis of the cross section of the vessel is a, and a semi-minor axis is b, a volume of the blood vessel 20 detected by the PPG sensor 1110B is about $\pi abL$. Because the volume $\pi abL$ of the oval blood vessel 20 is smaller than the volume $\pi r^2 L$ of the round blood vessel 20, the deformation of the blood vessels 20 reduce the total volume of the measured blood vessels 20, and the signal strength detected by the PPG sensor 1110B decreases. In an embodiment, impact on the detected PPG under different pressures may be obtained in advance, and a comparison table is established to record a compensation value required to compensate the impact. Therefore, the corresponding compensation value may be queried from the pre-stored comparison table based on a sensing result of the pressure sensor 1140, and then the PPG can be corrected.

Figure 7:
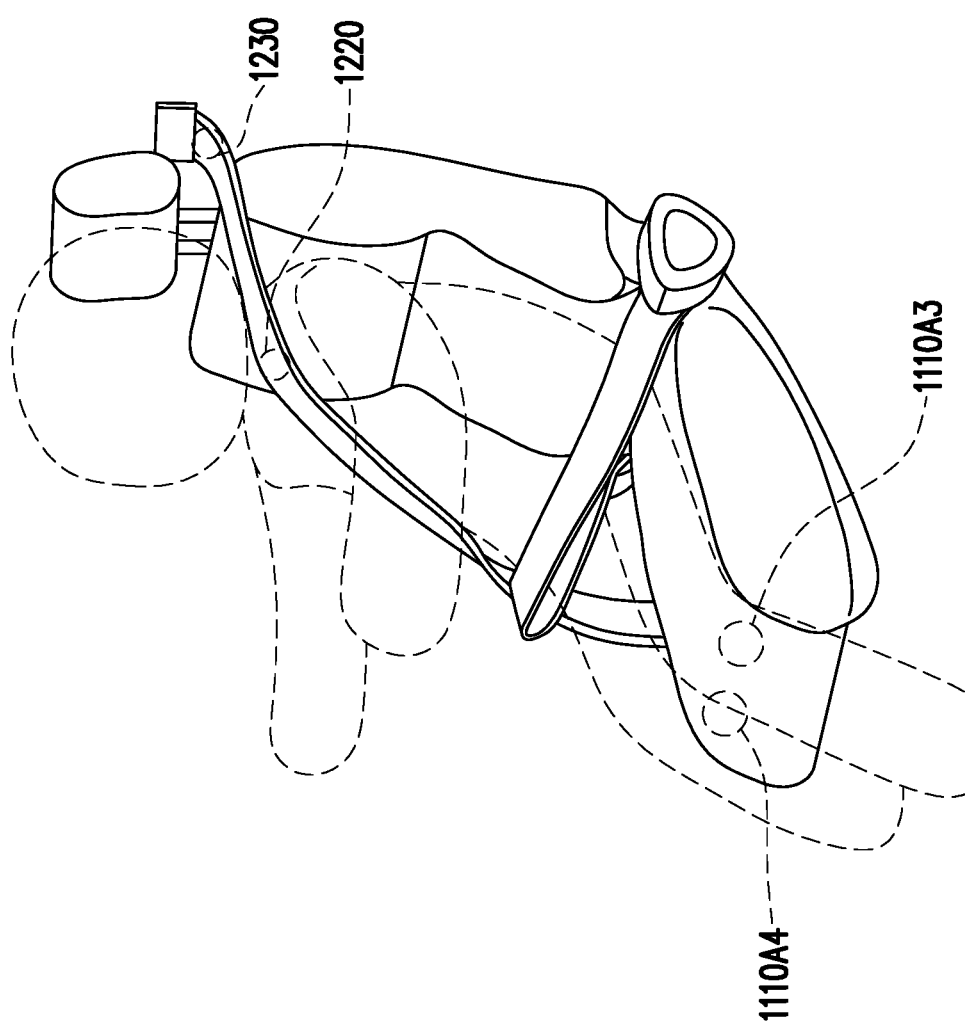
FIG. 7 is a schematic configuration diagram of a sensor of another part of the driving assistance system in FIG. 1.

FIG. 7 is a schematic configuration diagram of a sensor of another part of the driving assistance system in FIG. 1. Referring to FIG. 1 and FIG. 7, in the present embodiment, the ECG sensor 1110A may further include a third electrode 1110A3 disposed on the driver's seat of the vehicle to be in contact with one of the legs of the driver. The first electrode 1110A1, the second electrode 1110A2, and the third electrode 1110A3 that are in contact with the driver may constitute a three-lead ECG sensor 1110A, and provide an ECG including more information. For example, when arrhythmia is determined at block J114 in FIG. 3, the ECG may be provided by the three-lead ECG sensor 1110A to determine whether the ECG of the driver is normal at block J116. In addition, the ECG sensor 1110A may further include a reference electrode 1110A4 disposed on the driver's seat. The third electrode 1110A3 and the reference electrode 1110A4 are respectively in contact with the legs of the driver. In addition, a pressure sensor 1220 may be configured in a section that is of a seat belt and that is mainly used to bear the driver's pressure, so that when the body of the driver is weak and puts more pressure on the seat belt, a situation can be detected by the pressure sensor 1220. The tension sensor 1230 can be configured at an end of the seat belt, so that when the body of the driver is weak or twisted to pull the seat belt, a condition can be detected by the tension sensor 1230.

Figure 8:
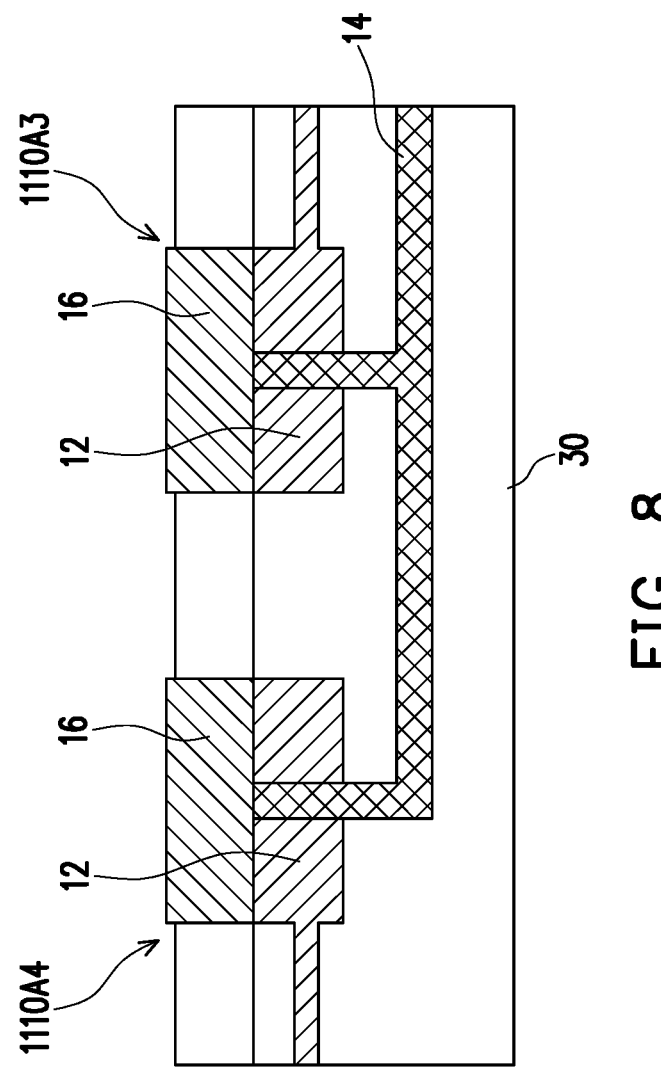
FIG. 8 is a schematic diagram of an electrode in FIG. 7.

FIG. 8 is a schematic diagram of an electrode in FIG. 7. Referring to FIG. 1 and FIG. 8, because the three-lead ECG sensor 1110A is not normally required, an electrical contact between the third electrode 1110A3 and the driver can be established only when required. In the present embodiment, the third electrode 1110A3 is configured at a seat cushion 30 of the driver's seat, and includes an electrode sheet 12, a conductive liquid pipe 14, and a moisture-permeable member 16. The processing device 1300 controls the conductive liquid pipeline 14 to transfer a conductive liquid to the moisture-permeable member 16. The moisture-permeable member 16 is configured to be in contact with and conduct the electrode sheet 12 and one of the legs of the driver through the conductive liquid. In other words, the conductive liquid is transferred to the moisture-permeable member 16 through the conductive liquid pipeline 14 as required. Even if the driver wears pants, skirts, or other clothing, the conductive liquid can wet a part in which the clothing is in contact with the moisture-permeable member 16, thereby establishing a conductive path between the electrode sheet 12 on the seat cushion 30 and one of the legs of the driver. In addition, the conductive fluid can have a quick-drying characteristic to facilitate the driver's seat to quickly return to an original state.

Figure 9B:
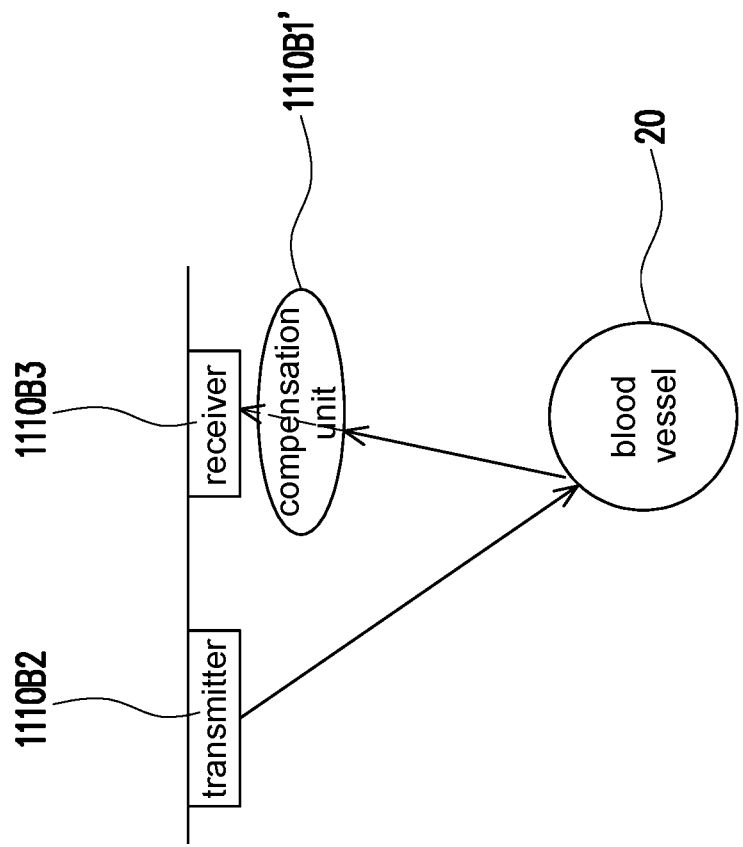
FIG. 9A and FIG. 9B are schematic diagrams of two PPG sensors of the driving assistance system in FIG. 1.
Figure 9A:
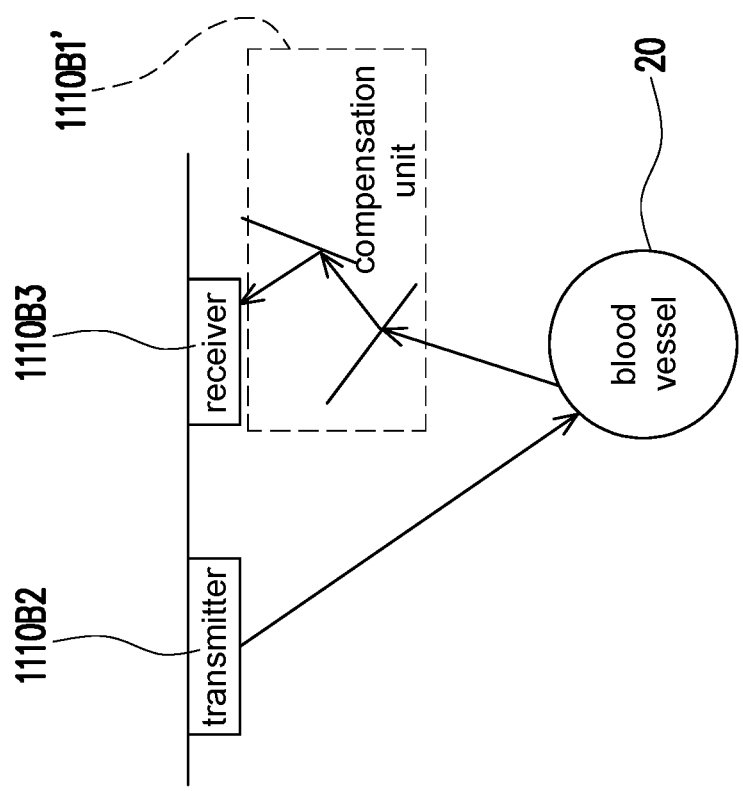

FIG. 9A and FIG. 9B are schematic diagrams of two PPG sensors of the driving assistance system in FIG. 1. Referring to FIG. 1, FIG. 9A, and FIG. 9B, in the present embodiment, the PPG sensor 1110B of the physiological information sensing system 1100 includes a transmitter 1110B2, a receiver 1110B3, and a compensation unit 1110B1'. The compensation unit 1110B1' in FIG. 9A is a phase retarder, and the compensation unit 1110B1' in FIG. 9B is a photointerrupter. In an embodiment not shown, the compensation unit 1110B1' may be an RC retarder. The compensation unit 1110B1' is configured to synchronize heart rate information in a PPG with heart rate information in an ECG. In addition, the heart rate information in the PPG and the heart rate information in the ECG may also be synchronized through an algorithm. According to detection principles of the PPG and the ECG, it can be found that a peak of the ECG is from contraction of the ventricle, and a peak of the PPG is caused by vasodilatation or vasoconstriction. Therefore, an occurrence time of a peak of the PPG and an occurrence time of a peak of the ECG are compared to obtain a time of transmitting blood from the heart to a measurement site, that is, a pulse transit time (PTT). A speed of pulse transit is directly related to a blood pressure. When the blood pressure is high, the pulse transit is fast; otherwise, the pulse transit is slow. Therefore, a pulse transit time of the driver obtained in advance can be used to synchronize the heart rate information in the PPG with the heart rate information in the ECG through the algorithm or the RC retarder. In addition, the phase retarder or the photointerrupter may be used to delay the occurrence time of the peak of the PPG, so that the heart rate information in the PPG and the heart rate information in the ECG can also be synchronized.

Figure 10:
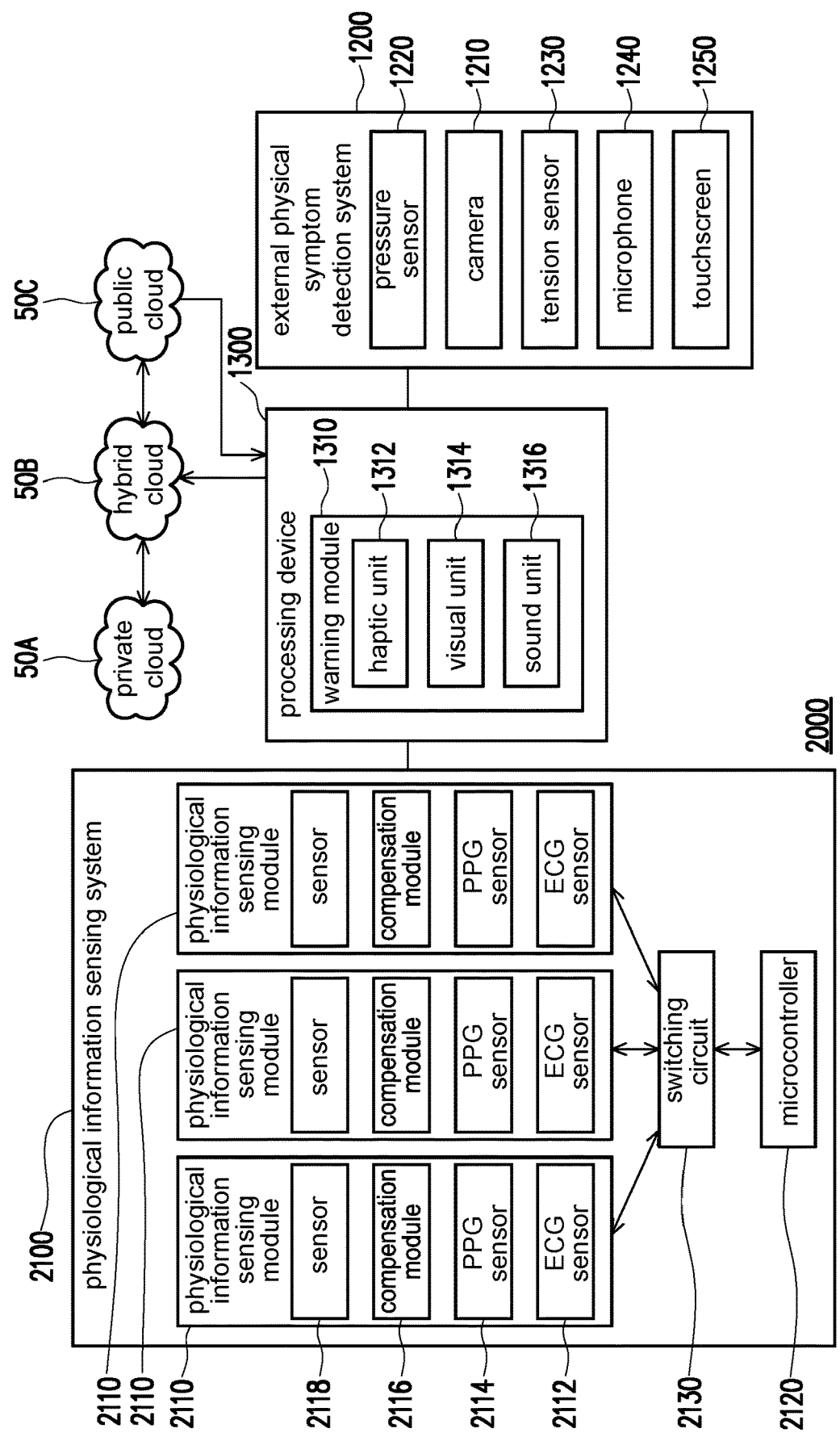
FIG. 10 is a schematic diagram of an architecture of a driving assistance system according to another embodiment of the disclosure.

FIG. 10 is a schematic diagram of an architecture of a driving assistance system according to another embodiment of the disclosure. Referring to FIG. 10, a driving assistance system 2000 in the present embodiment is similar to the driving assistance system in FIG. 1. Some same details are not described herein again, and the foregoing various changes regarding the driving assistance system in FIG. 1 can also be applied to the driving assistance system 2000 in the present embodiment. The driving assistance system 2000 in the present embodiment includes a physiological information sensing system 2100 and a processing device 1300, that is, does not include an external physical symptom detection system, but may also include the same external physical symptom detection system 1200 as that shown in FIG. 1. The physiological information sensing system 2100 is configured to sense physiological information of a driver. The processing device 1300 is coupled to the physiological information sensing system 2100. When the physiological information of the driver is abnormal, the processing device initiates an emergency procedure.

The physiological information sensing system 2100 includes a plurality of physiological information sensing modules 2110, a microcontroller 2120, and a switching circuit 2130. The plurality of physiological information sensing modules 2110 are configured in at least one operation portion of a vehicle shown in FIG. 4 and coupled to the switching circuit 2130. The microcontroller 2120 is coupled to the switching circuit 2130 and the processing device 1300. The microcontroller 2120 controls the switching circuit 2130 to transmit, to the processing device 1300, the physiological information detected by the physiological information sensing module 2110 that is configured in the at least one operation portion and that is in contact with the driver.

Figure 11:
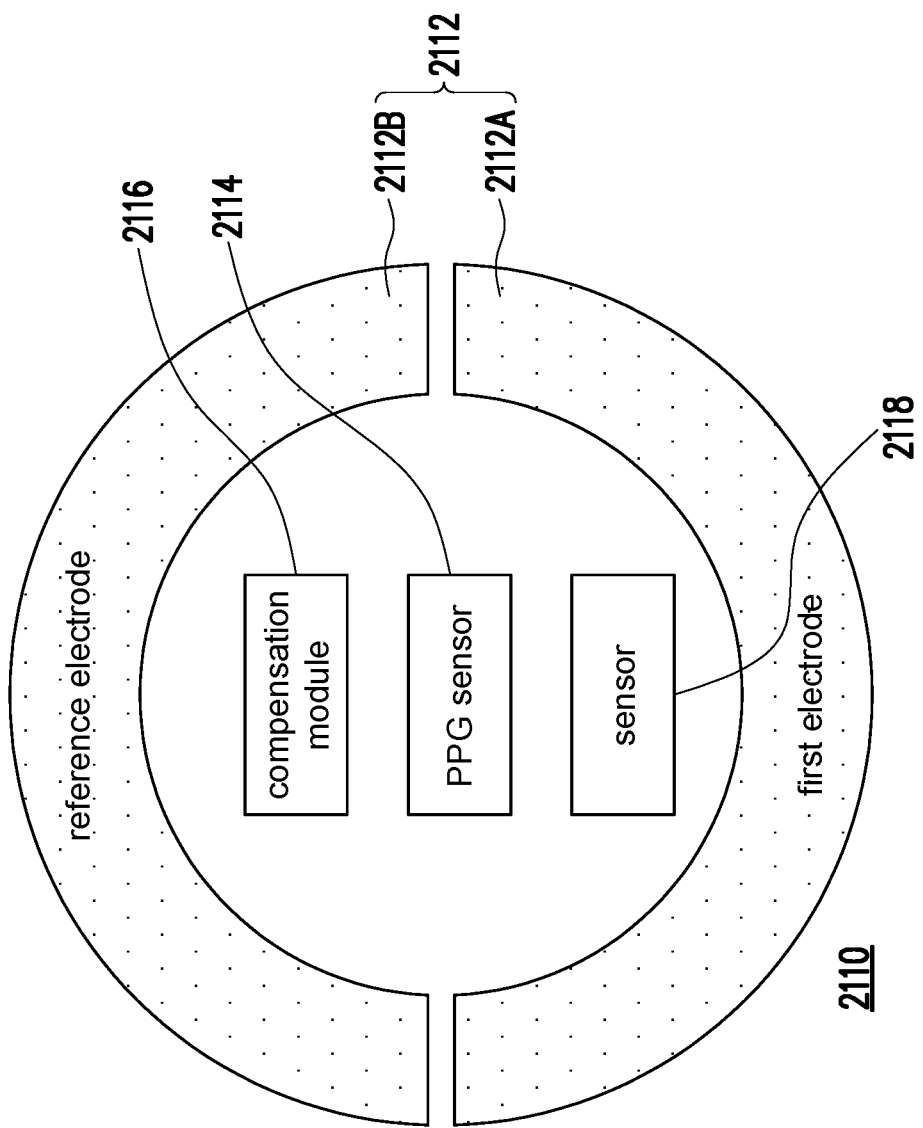
FIG. 11 is a schematic diagram of a physiological signal sensing module of the driving assistance system in FIG. 10.

FIG. 11 is a schematic diagram of a physiological signal sensing module of the driving assistance system in FIG. 10. Referring to FIG. 11, each of the physiological information sensing modules 2110 includes an ECG sensor 2112, a PPG sensor 2114, and a compensation module 2116. The microcontroller 2120 chooses to perform ECG sensing mode measurement or PPG sensing mode measurement through the switching circuit 2130. The ECG sensor 2112 includes, for example, one first electrode 2112A and one reference electrode 2112B. In addition, each of the physiological information sensing modules 2110 may optionally further include another sensor 2118, and the sensor 2118 may be a body temperature-sweat sensor. The compensation module 2116 may be a skin impedance sensor 1150, a pressure sensor 1140, a compensation unit (a phase retarder, a photointerrupter, or an RC retarder), or the like in FIG. 1.

Figure 12:
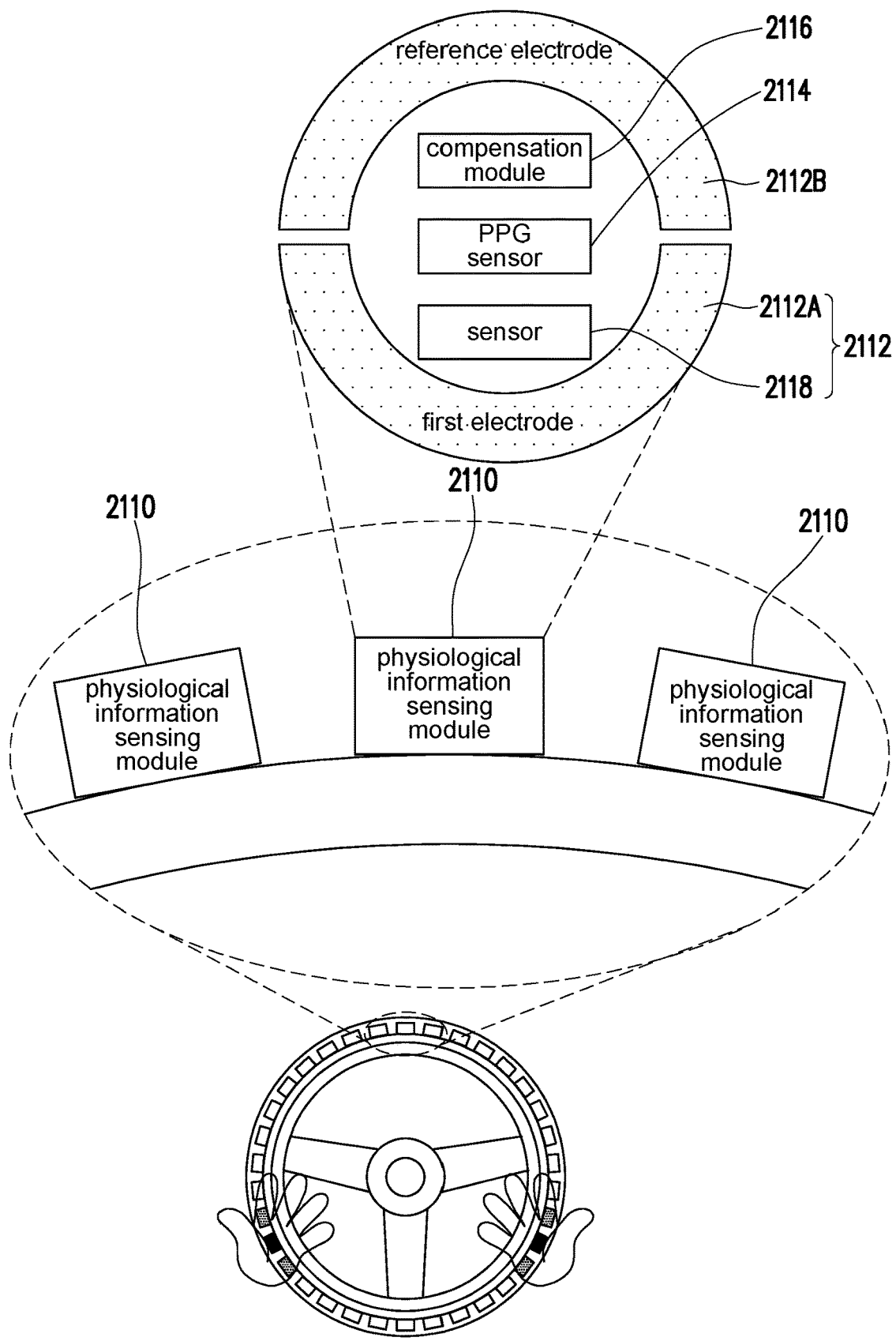
FIG. 12 is a schematic diagram of a relative position between a palm and a physiological signal sensing module when a driver holds a steering wheel in the driving assistance system in FIG. 10 according to an embodiment of the disclosure.

In the driving assistance system 2000 in FIG. 10, the physiological information sensing module 2110 includes both the ECG sensor 2112 and the PPG sensor 2114, and therefore may choose to perform ECG sensing mode measurement or PPG sensing mode measurement based on an actual situation. FIG. 12 is a schematic diagram of a relative position between a palm and a physiological signal sensing module when a driver holds a steering wheel in the driving assistance system in FIG. 10 according to another embodiment of the disclosure. Referring to FIG. 12, when the driver holds the steering wheel, each palm of the driver may be in contact with at least one complete physiological information sensing module in the plurality of physiological information sensing modules 2110 placed on the steering wheel. When the driver is in contact with two or more physiological information sensing modules 2110, for example, left and right hands of the driver each are in contact with one complete physiological information sensing module 2110, an ECG sensing mode is activated to obtain more accurate physiological information of the driver. When the driver is in contact with only one ECG sensor (a single-lead loop cannot be formed), a PPG sensing mode is activated, and the PPG sensor 2114 measures a PPG of the driver. In this way, the physiological information of the driver can be obtained even if the driver operates the steering wheel with one hand.

Figure 13:
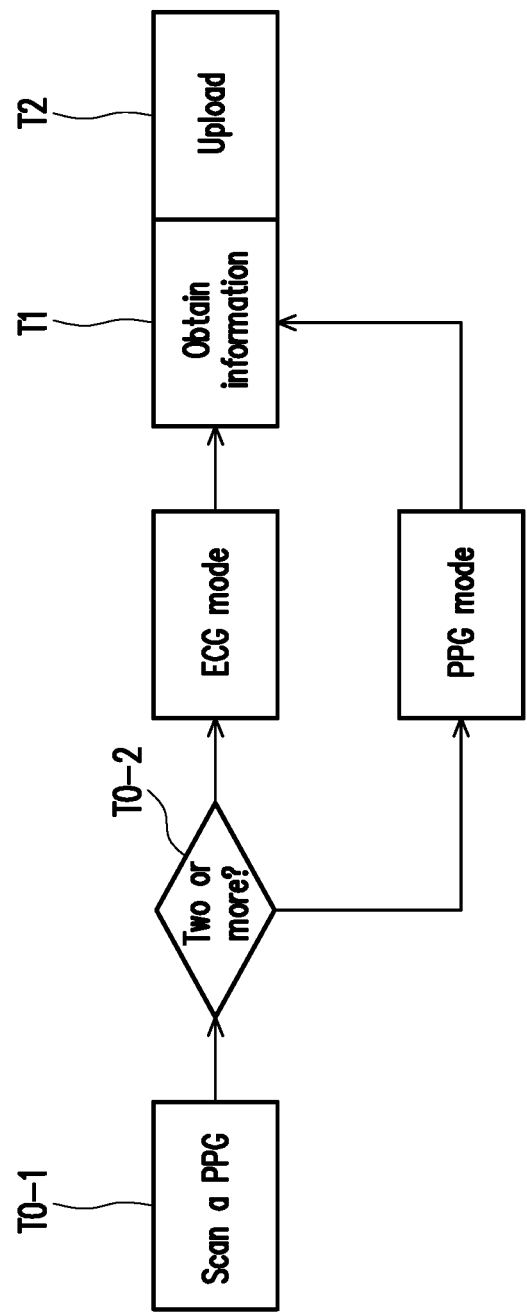
FIG. 13 illustrates a physiological signal sensing procedure in a driving assistance method according to an embodiment of the disclosure.

FIG. 13 illustrates a physiological signal sensing procedure in a driving assistance method according to an embodiment of the disclosure. Referring to FIG. 10 and FIG. 13, at a time T0-1, it is first determined, through scanning, whether a PPG can be sensed. At a time T0-2, it is determined whether there are two or more physiological information sensing modules 2110 that can sense the PPG, that is, whether there are two physiological information sensing modules 2110 that can provide an ECG. If there are two or more, the physiological information sensing system switches to ECG sensing mode measurement before the time T1. If there are no two or more physiological information sensing modules, the physiological information sensing system switches to PPG sensing mode measurement before the time T1. Then, at the time T1, the physiological information is obtained, which may be the ECG, the PPG, or both the ECG and the PPG. Finally, the physiological information is transmitted to the processing device 1300 at the time T2 and uploaded to the hybrid cloud 50B when necessary.

Taking the driver holding the steering wheel with both hands as an example, in the ECG sensing mode, for example, a first physiological signal sensing module 2110 that is in contact with one hand of the driver is identified through a galvanic skin response (GSR), and the physiological signal sensing module 2110 is set to "positive". Then, for example, searching is performed down in a clockwise manner sequentially until a physiological signal sensing module 2110 that is in contact with the other hand of the driver is identified, and the physiological signal sensing module 2110 is set to "negative". In this way, the two physiological signal sensing modules 2110 and a body of the driver can form a single-lead loop to measure the ECG.

In view of the above, in the driving assistance system and the driving assistance method in the disclosure, whether the physiological information and the external physical symptom are normal can be determined. Accordingly, the emergency procedure can be timely and accurately initiated to reduce the probability of an accident. Optionally, the physiological information may include at least one of the ECG and the PPG to ensure accuracy of the sensed physiological information. The physiological information and the external physical symptom may be sensed and detected at the same time, or the external physical symptom may be detected after it is determined, through sensing, that the physiological information is abnormal, to determine the kind of physical discomfort the driver is experiencing.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A driving assistance system, comprising:
a physiological information sensing system configured to sense physiological information of a driver;
an external physical symptom detection system configured to detect an external physical symptom of the driver; and
a processing device coupled to the physiological information sensing system and the external physical symptom detection system, wherein when the physiological information of the driver and the external physical symptom of the driver are abnormal, the processing device initiates an emergency procedure,
wherein the physiological information sensing system comprises a plurality of physiological information sensing modules, each of the plurality of physiological information sensing modules comprises an ECG sensor, a photoplethysmogram (PPG) sensor, and a compensation module, the compensation module comprises a phase retarder, a photointerrupter, or a resistance-capacitance (RC) retarder configured to synchronize heart rate information in a PPG provided by the PPG sensor with heart rate information in an ECG provided by the ECG sensor.

2. The driving assistance system according to claim 1, wherein the physiological information sensing system and the external physical symptom detection system simultaneously and continuously monitor the physiological information of the driver and the external physical symptom of the driver; or
the physiological information sensing system is activated first, and then the external physical symptom detection system is activated when the physiological information of the driver is abnormal.

3. The driving assistance system according to claim 1, wherein the external physical symptom detection system is activated first, and then the physiological information sensing system is activated when the external physical symptom of the driver is abnormal.

4. The driving assistance system according to claim 1, wherein the physiological information sensing system further comprises a microcontroller, and a switching circuit, the plurality of physiological information sensing modules being configured in at least one operation portion of a vehicle and coupled to the switching circuit, the microcontroller being coupled to the switching circuit and the processing device, and the microcontroller controlling the switching circuit to transmit, to the processing device, the physiological information detected by the physiological information sensing module that is configured in the at least one operation portion and that is in contact with the driver.

5. The driving assistance system according to claim 4, wherein the at least one operation portion is a steering wheel of the vehicle and comprises at least three of the physiological information sensing modules within a range of 70 millimeter (mm).

6. The driving assistance system according to claim 4, wherein the at least one operation portion comprises at least two of a steering wheel, a start button, a gear stick, a cockpit door, and a hand brake.

7. The driving assistance system according to claim 1, wherein when the external physical symptom of the driver is abnormal and after the abnormality lasts for a preset period of time, the processing device initiates the emergency procedure.

8. The driving assistance system according to claim 1, wherein a plurality of first electrodes or a plurality of second electrodes of the ECG sensor being configured on a steering wheel of a vehicle and at least three of the plurality of first electrodes or the plurality of second electrodes being disposed within a range of 70 mm.

9. The driving assistance system according to claim 8, wherein the plurality of second electrodes of the ECG sensor are configured on the steering wheel, a start button, a gear stick, a cockpit door, or a hand brake of the vehicle.

10. The driving assistance system according to claim 8, wherein a third electrode of the ECG sensor is disposed on a driver's seat of the vehicle to be in contact with one of legs of the driver, and a reference electrode of the ECG sensor is disposed on the driver's seat, the third electrode and the reference electrode being respectively in contact with the legs of the driver.

11. A driving assistance method, comprising:
detecting physiological information of a driver by using a physiological information sensing system comprising a plurality of physiological information sensing modules, wherein each of the plurality of physiological information sensing modules comprises an ECG sensor, a photoplethysmogram (PPG) sensor, and a compensation module, the compensation module comprises a phase retarder, a photointerrupter, or a resistance-capacitance (RC) retarder configured to synchronize heart rate information in a PPG provided by the PPG sensor with heart rate information in an ECG provided by the ECG sensor;
detecting an external physical symptom of the driver; and
initiating an emergency procedure when the physiological information of the driver and the external physical symptom of the driver are abnormal.

12. The driving assistance method according to claim 11, wherein the physiological information comprises an electrocardiogram (ECG) or a photoplethysmogram (PPG), and the external physical symptom comprises at least one of an expression, a gesture, speech, and an action.

13. The driving assistance method according to claim 11, wherein the physiological information sensing system and an external physical symptom detection system simultaneously and continuously monitor the physiological information of the driver and the external physical symptom of the driver; or
the physiological information sensing system is activated first, and then the external physical symptom detection system is activated when the physiological information of the driver is abnormal.

14. The driving assistance method according to claim 11, wherein an external physical symptom detection system is activated first, and then the physiological information sensing system is activated when the external physical symptom of the driver is abnormal.

15. The driving assistance method according to claim 11, wherein the emergency procedure comprises at least one of issuing a warning, autonomous driving, reporting to police, pulling over, and going to hospital.

16. The driving assistance method according to claim 11, wherein the step of detecting the physiological information of the driver comprises: using the plurality of physiological information sensing modules respectively configured in at least one operation portion of a vehicle, and obtaining the physiological information detected by the physiological information sensing module that is configured in the at least one operation portion and that is in contact with the driver.

17. The driving assistance method according to claim 11, wherein when the external physical symptom of the driver is abnormal and after the abnormality lasts for a preset period of time, a processing device initiates the emergency procedure.

18. The driving assistance method according to claim 11, wherein the physiological information of the driver is corrected based on at least one of a pressure value and skin impedance of a detected part of the driver.

19. A driving assistance system, comprising:
a physiological information sensing system configured to sense physiological information of a driver; and
a processing device coupled to the physiological information sensing system, wherein when the physiological information of the driver is abnormal, the processing device initiates an emergency procedure,
wherein the physiological information sensing system comprises a plurality of physiological information sensing modules, a microcontroller, and a switching circuit, the plurality of physiological information sensing modules being configured in at least one operation portion of a vehicle and coupled to the switching circuit, the microcontroller being coupled to the switching circuit and the processing device, and the microcontroller controlling the switching circuit to transmit, to the processing device, the physiological information detected by the physiological information sensing module that is configured in the at least one operation portion and that is in contact with the driver,
wherein each of the physiological information sensing modules comprises an electrocardiogram (ECG) sensor, a photoplethysmogram (PPG) sensor, and a compensation module, and the microcontroller chooses to perform ECG sensing mode measurement or PPG sensing mode measurement through the switching circuit,
wherein the compensation module comprises a phase retarder, a photointerrupter, or a resistance-capacitance (RC) retarder configured to synchronize heart rate information in a PPG provided by the PPG sensor with heart rate information in an ECG provided by the ECG sensor.

* * * * *